United States Patent [19]

Skrabal

[11] Patent Number: 5,066,283
[45] Date of Patent: Nov. 19, 1991

[54] DEVICE FOR THE WITHDRAWAL AND STORAGE OF INDIVIDUAL FLUID FRACTIONS LATHERED AT GIVEN INTERVALS

[75] Inventor: Falko Skrabal, Graz, Austria

[73] Assignee: AVL AG, Schaffhausen, Switzerland

[21] Appl. No.: 348,488

[22] PCT Filed: Jul. 11, 1988

[86] PCT No.: PCT/AT88/00051
§ 371 Date: Mar. 8, 1989
§ 102(e) Date: Mar. 8, 1989

[87] PCT Pub. No.: WO89/00397
PCT Pub. Date: Jan. 26, 1989

[30] Foreign Application Priority Data

Jul. 9, 1987 [AT] Austria .................. 1732/87

[51] Int. Cl.⁵ .............................. A61M 1/00
[52] U.S. Cl. ........................ 604/152; 604/27; 128/762
[58] Field of Search ............... 604/131, 149, 151, 152, 604/153, 48, 51, 65, 66, 67, 18, 19, 27; 128/762

[56] References Cited

U.S. PATENT DOCUMENTS

| | | | |
|---|---|---|---|
| 3,429,313 | 2/1969 | Romonelli | 604/152 |
| 3,616,789 | 11/1971 | Grabhorn | 128/762 |
| 3,674,011 | 7/1972 | Michel et al. | 128/762 |
| 3,765,402 | 10/1973 | Grabhorn | 128/762 |
| 4,077,395 | 3/1978 | Woolner | 128/762 |
| 4,705,500 | 11/1987 | Reimels et al. | 604/22 |

Primary Examiner—C. Fred Rosenbaum
Assistant Examiner—Corrine Maglione
Attorney, Agent, or Firm—Watson, Cole, Grindle & Watson

[57] ABSTRACT

A device for withdrawing body fluids such as blood, urine and tissue fluid includes a withdrawal unit, a suction unit, and a storage system receiving the body fluid between the withdrawal unit and the suction unit, the storage system being divided into separate areas holding the fluid fractions gathered at given intervals and permitting the individual fluid fractions to be identified with regard to their time of withdrawal. In this way tests requiring repeated sampling at short intervals are made easier for doctor and patient.

18 Claims, 3 Drawing Sheets

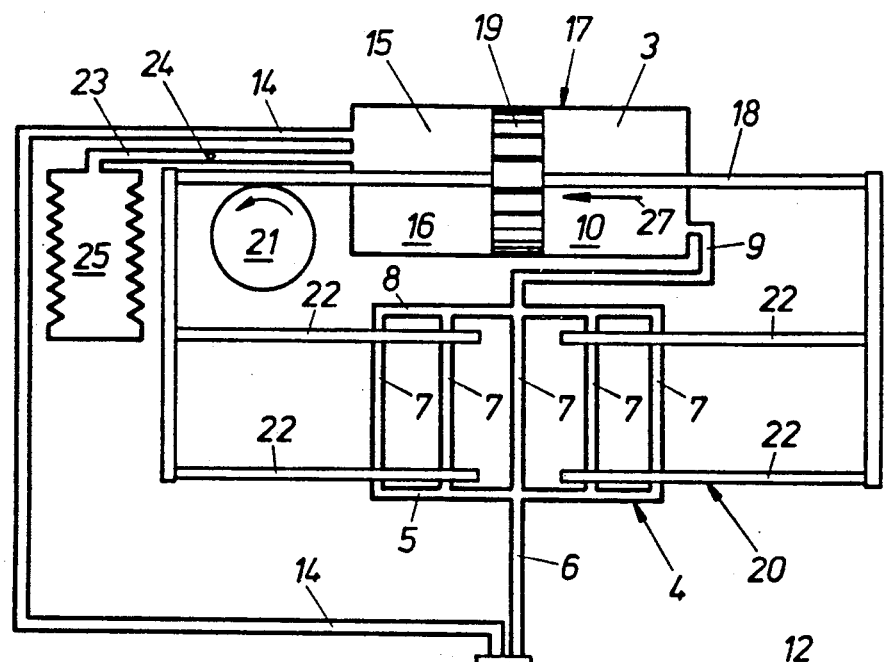
Fig. 1
Fig. 1a
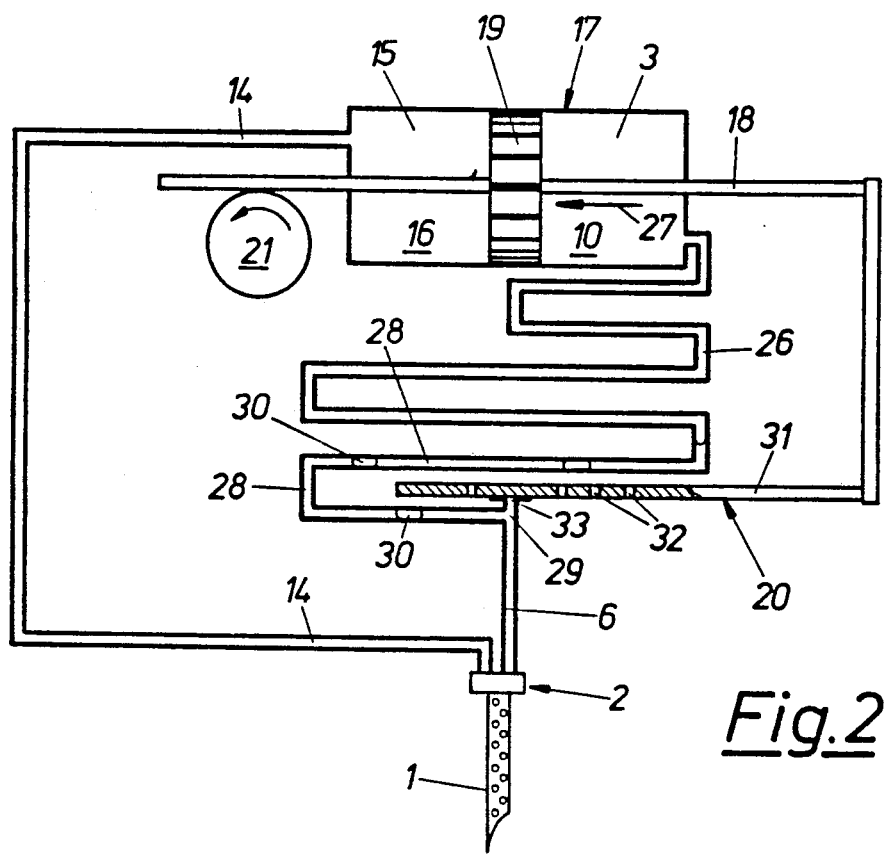
Fig. 2

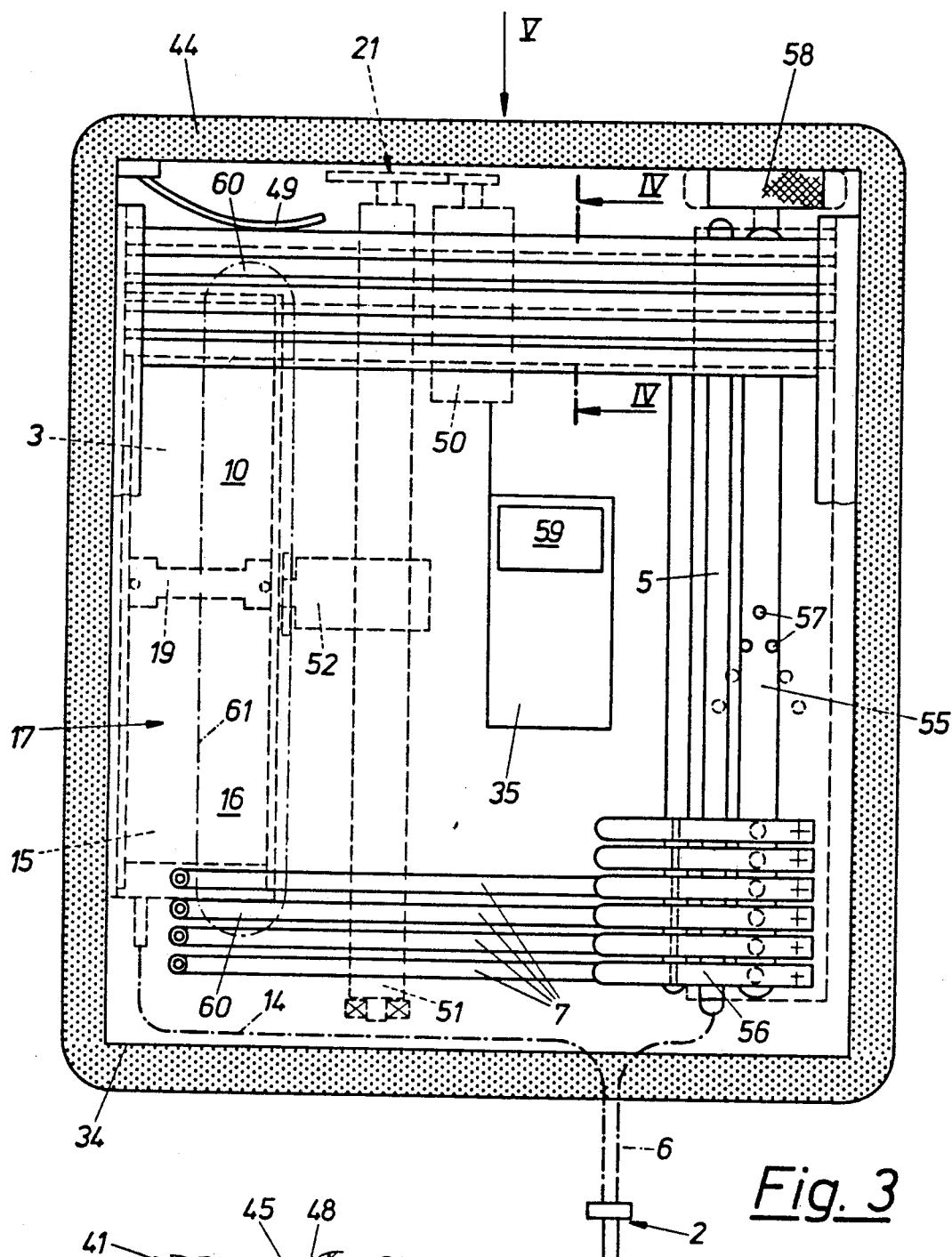
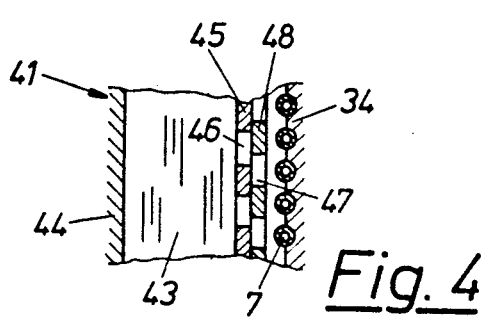
Fig. 3
Fig. 4

DEVICE FOR THE WITHDRAWAL AND STORAGE OF INDIVIDUAL FLUID FRACTIONS LATHERED AT GIVEN INTERVALS

BACKGROUND OF THE INVENTION

This invention relates to a device for withdrawing body fluids such as blood urine, and tissue fluid, which includes a withdrawal unit and a suction unit.

DESCRIPTION OF THE PRIOR ART

For withdrawing body fluids, such as blood, tissue fluid, fluid from body cavities, or urine, various medical devices are known, the most common being piston-fitted syringes, pipettes, and cannulas and catheters remaining at the site of withdrawal.

In many instances the parameter or parameters of the body fluid relevant for the particular test must be measured or monitored for a given period of time; in view of the rapid changes that often occur in parameters, it is frequently necessary to draw and analyze a sample of the body fluid at short intervals.

In certain hormone tests, for instance, blood samples must be taken every hour, which is extremely unpleasant for both patient and doctor, especially during the night. Examples in which blood sampling is required in order to obtain diurnal variation profiles include a number of hormone disorders, such as morbus cushing with disturbances in the diurnal cortison rhythm disturbances of growth and pubescence characterized by an absence of the nocturnal peaks of growth and sex hormones, and many others.

Another important application is the pharmaceutical industry, in which blood and tissue levels of drugs or their effects must be registered over a period of 24 hours.

In some instances it is possible to take blood samples via permanent arterial or venous access paths, which will at least avoid repeated puncturing several times a day; the patient still has to put up with unpleasant manipulations, however.

SUMMARY OF THE INVENTION

It is the object of this invention to propose a device for withdrawing body fluids which will relieve the patient from unpleasant manipulations and limit the work load of the medical staff, while permitting the parameters to be analyzed as well as their variations over time to be determined with adequate precision and identified with regard to their time of withdrawal.

According to the invention this is achieved by providing a storage system between the withdrawal unit and the suction unit, which is designed for receiving the body fluid and contains individual areas which may be separated from each other and hold the fluid fractions gathered at certain intervals, and which permit these individual fluid fractions to be clearly identified with regard to their time of withdrawal. In all tests in which an on-line analysis of the body fluid gathered is not possible for various reasons, the device described by the invention permits an analysis of the individual parameters of interest linked to the time of fluid removal, even at the end of an extended sampling process. A suitable withdrawal device is either a needle inserted in the blood stream, or a catheter, or a cannula in the catheter or as a branch-off—for instance, if urine is to be sampled. Suitable suction devices are all pumps generating a constant negative pressure, such as a roll diaphragm pump or other devices, for example vacuum connections.

A first variant of the invention may provide that the storage system be configured as a flexible tube connecting the withdrawal unit and the suction unit, and that a control unit be located at the inlet end of the tube in order to separate the individual fluid fractions, via which control unit a gaseous medium separating the individual fluid fractions can be introduced into the tube at given time intervals. This control unit may be configured as a valve connecting the storage system to the outside air after given periods of time, such that an air bubble can be sucked into the tube of the storage system, thus separating the individual fluid fractions.

Another variant of the invention provides that the withdrawal unit be connected to a distributor, and that parallel branch lines from this distributor be provided for the individual separable areas of the storage system, a control unit connecting these branch lines to the withdrawal unit one at a time, and all branch lines being connected to the suction unit via a manifold. In this variant each fluid fraction is only in contact with one specific branch line, which will largely eliminate the danger of a mixture or carryover of components of other fluid fractions.

In a preferred variant of the invention the withdrawal unit is provided with an ingoing line for a liquid to be introduced into the body, in addition to an outgoing line for the body fluid to be gathered, the ingoing line being connected to a pressure unit. With this variant it is possible to apply an agent preventing blood clotting, for example heparin, via the ingoing line of the withdrawal unit, which agent is continuously supplied by means of a pressure unit in the dose required for the blood sample.

For applications directly in the tissue the invention may provide that the withdrawal unit be configured as a subcutaneous needle/catheter, or vascular needle, with two concentric channels or lumes, whose one lumen is connected to the ingoing line while the other one is connected to the outgoing line. In this variant a perfusion liquid is applied directly into the tissue, and is gathered by fractions after its partial equilibration with the tissue parameters of interest, and finally analyzed for the parameters of interest. The use of endogenous or exogenous markers is recommended in order to determine the degree of interaction between perfusion liquid and tissue and to take it into account during the subsequent analysis. Equilibration needs to be only partial, since the perfusion liquid is analyzed with regard to both the parameter of interest and the characteristics of the endogenous or exogenous markers.

The subcutaneous needle or catheter may have an inner cannula connected to the outgoing line, which is surrounded by an outer cannula with openings towards the tissue, the latter being connected to the ingoing line. The device described can be used for determining, from the liquid fractions obtained, the tissue level of a hormone, or a substrate, such as blood sugar, or a drug, predominant at the time of withdrawal of the individual fractions.

In a simple device according to the invention the suction unit and the pressure unit are configured as a reciprocating pump, which is provided on the pressure side with a reservoir connected to the ingoing line and containing the liquid to be introduced into the body, and, on the suction side, with a suction chamber connected to the storage system. In the instance of applications differing with regard to their suction and pressure volumes, compensation vessels with concertina walls may be provided, which communicate either with the pressure-side or the suction-side part of the reciprocating pump. In the invention, the device may be provided with a receiving vessel for this purpose, preferably of variable capacity, which is connected to the reservoir for the liquid to be introduced into the body via a flow-regulating element. In this manner lesser amounts of liquid may be injected while fully maintaining suction power. For example, in applications necessitating the feeding of heparin, the ration of outgoing blood and ingoing heparin is between 10:1 and 500:1.

In order to simplify cleaning and handling of the device described by the invention, the proposal is put forward that the drive of the suction and pressure device as well as that of the control unit of the storage system, along with the corresponding control electronics, be located in a main housing, and that the storage system receiving the body fluid, and the suction/pressure units along with their connecting lines be located in a case which is detachable from the main housing. All components of the device in touch with the body fluid may be removed together with the case and may be replaced by another one. It has proved of advantage to use a U-shaped case, whose halves are situated one on either side of the main housing, each including a number of individual branch lines. For instance, branch lines may be provided for a total of 48 fluid fractions, ensuring a 24 hour test operation with fluid withdrawal every 30 minutes.

Since some body fluids to be gathered, or rather, their components, have high temperature sensitivity, it is proposed that the case containing the storage system, or rather, its halves be connected to an adjustable cooling unit, which has a container for a cooling gel, and whose wall facing the storage system has openings that are preferably regularly spaced, the cross-sections of these openings, which are controlled by a thermostat, admitting cooling air into the storage system. In this manner the individual fluid fractions are cooled to the required temperature until they are analyzed. Via the thermostat-controlled cross-sections of the openings the diminishing cooling effect of the cooling gel may be compensated.

In order to further simplify the device described by the invention, only one driving motor may be provided, actuating the suction and pressure device by means of a spindle drive and driving a camshaft via a reducing gear and a ratchet wheel. The cams of the noted camshaft cooperate with squeezer levers of the control unit attached to the main housing, each such cam-lifted lever giving access to one of the branch lines. No additional parts are required that would complicate the mechanism. It is also possible, of course, to locate the squeeze-off elements cooperating with the camshaft in the detachable case.

In order to be able to analyze the individual fractions they must be removed from the device and filled into individual test tubes. For this purpose the invention provides that the drive of the suction and pressure device may be reversed in order to permit removal of the individual fluid fractions from the storage system. In this instance the suction unit is converted into a pressure unit releasing the individual fluid fractions via the withdrawal system, i.e., needle or cannula.

Of course, the individual fluid fractions can also be tapped via a knob or crank cooperating with the suction/pressure device and the control unit of the storage system.

In order to efficiently prevent the individual fluid fractions from mixing—especially when they are separated by air bubbles—the invention proposes that the diameters of the branch lines, or rather, the flexible tube be kept small, such that adhesive forces acting between the inner walls of the storage system and the body fluid are larger than exterior forces acting upon the device, such as gravitation or additional accelerating forces. The diameters of the lines containing the fluid fractions should be selected such that the individual fractions are held in place by adhesive forces and remain in the place once defined in the storage system, no matter where the individual lines are situated, or which accelerating forces are acting upon them.

The invention finally provides that an electronic control system be provided with a display for entering a sequencing program. In this way the individual fractions of the fluid can be removed at individual, preselected points in time.

DESCRIPTION OF THE DRAWINGS

Following is a more detailed description of the invention as illustrated by the accompanying drawings, in which FIG. 1 shows a device as disclosed by the invention,
FIG. 1a a detail A from FIG. 1,
FIG. 2 another device according to the invention,
FIG. 3 a variant according to FIG. 1,
FIG. 4 a section along line IV—IV in FIG. 3,
FIG. 5 a view from above, in the direction of arrow V in FIG. 3, parts of the cooling unit having been removed.

DETAILED DESCRIPTION OF THE PREFERRED EMBODIMENTS

Figure 5:
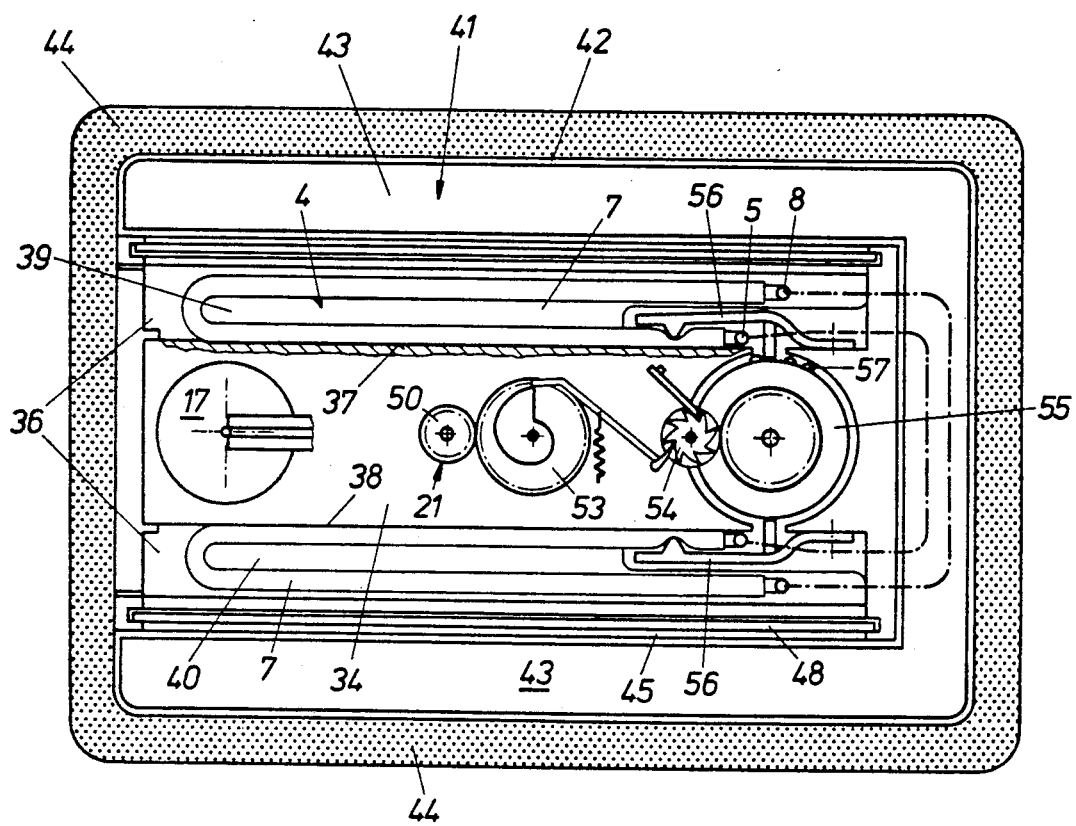

A device for withdrawing fluids from the body is shown schematically in FIG. 1. Between a withdrawal unit 2 configured as a subcutaneous needle or vascular needle 1 with two concentric channels, and a suction unit 3, there is situated a storage system 4 receiving the fluid fractions obtained. Departing from a distributor 5, which is connected with the outgoing line 6 of the withdrawal unit 2, the storage system 4 comprises a number of parallel branch lines 7 which are connected with the suction chamber 10 of the suction unit 3 via a manifold 8 and a connecting line 9 departing therefrom.

As is seen from detail A of FIG. 1 presented in FIG. 1a, the withdrawing unit 2 may be configured as a two-channel subcutaneous needle 1 whose inner channel 11 is in contact with the outgoing line 6, while the outer channel 13, which contains openings 12, is in contact with an ingoing line 14. The ingoing line 14 is connected to a reservoir 16 of a pressure unit 15, from which reservoir 16 a liquid to be introduced into the body, e.g., a perfusion liquid or an agent preventing blood clotting, etc., can be fed into the withdrawal unit 2.

Of course, the pressure unit 15, the ingoing line 14 and the two-channel needle 1 need not be included in a device which is only used for withdrawing blood; in this instance a conventional injection needle will suffice as a withdrawing device, or if a two-channel needle is used, the outer cannula need not have openings 12, since the blood is drawn trough the front opening of the needle. The inner cannula 11, which does not quite reach the tip of the outer cannula 13, may be used for adding an anticoagulant to the blood sample, for instance heparin.

A small number of openings 12 next to the tip of the outer cannula 13, can be of advantage in order to ensure that blood is drawn even if the front opening of the cannula touches the wall of the blood vessel.

In the variant shown here the suction unit 3 and the pressure unit 15 are combined in a reciprocating pump 17 whose suction chamber 10 is separated from the reservoir 16 by a piston 19 actuated by a driving rod 18.

By means of a control device 20 the branch lines 7 are connected to the outgoing line 6 one at a time, the control device 20 being in connection with the driving rod 18 of the piston pump 17 via a mechanical coupling (only shown schematically here), and being actuated together with the pump via a common drive 21. The arms 22 of the control device 20 are used to press shut both ends of those branch lines 7 that should not be opened to the body fluid.

Via a further line 23, in which is located a flow-control element 24, a variable capacity receiving vessel 25 is connected to the reservoir 16. Via the flow-control element 24 the amount of liquid flowing from the reservoir 16 into the ingoing line 14 may be varied while maintaining full suction power.

If the piston 19, and thus the control device 20, moves in the direction of the arrow 27, a partial vacuum is generated in the suction chamber 10, by which body fluid is pushed into the branch line opened by the control unit 20. If piston and control unit continue moving, this particular branch line is eventually pressed shut by the arms 22 of the control unit 20, and the branch line nearest in the direction of the arrow is opened. For drainage of the individual fluid fractions from the branch line 7 the drive unit simply is reversed.

In all subsequent variants identical parts have identical reference numbers. FIG. 2, for instance, shows a variant in which the storage system 4 is configured as a flexible tube 26 connecting the withdrawal unit 2 and the suction unit 3. In order to separate the individual fluid fractions 28, a control element 20 is placed next to the tube inlet 29, by means of which element 20 a medium separating the fluid fractions, for instance gas bubbles, may be introduced at given time intervals.

The control element 20 is presented schematically by an arm 31 with openings 32 uncovering an opening 33 in the vicinity of the tube inlet 29 as the control element continues moving in the direction of the arrow 27, upon which air from the environment is admitted briefly.

If the entrance of air or air/oxygen is undesirable, any other gas—provided that it does not affect the individual fluid fractions—may be introduced by means of such a control element, the only requirements being a suitable container and a feeder line.

Both in the variant of FIG. 1 and in that of FIG. 2 the control element 20 may be provided with a separate drive, for instance, a solenoid valve could be used, particularly in the variant of FIG. 2.

The variant shown in FIGS. 3 to 5 has a main housing 34 containing the drive 21 of the suction/pressure device configured as a reciprocating pump 17, and the corresponding control electronics 35 as well as a case 36 detachable from the main housing 34, in which are located the storage system 4, the suction and pressure units 3 and 15, and their connecting lines 5,6,8,14.

As is shown in FIG. 5, the case 36 is U-shaped, its halves 39, 40 being situated one on either side 37, 38 respectively, of the main housing 34, each half containing twenty-four single branch lines 7 with a capacity of 1 ml per line approximately. It is also possible to have cases 36 whose branch lines 7 have a capacity of 0.5 ml or 2 ml each, thus being suitable for the treatment of either children or grown-ups. The volume increase is obtained simply by increasing the number of windings of the branch lines 7, the cross-sections of the lines remaining small.

It is also possible, of course, to provide moulded channels for the individual fluid fractions, which are directly integrated in the case 36 and are furnished with a diaphragm in one particular place, which is acted upon by a squeezing element.

The case halves 39 and 40 containing the storage system 4 are surrounded by a cooling unit 41 shown in FIGS. 4 and 5, whose housing 42 is filled with a cooling gel 43. In order to safeguard continous cooling of the fluid fractions in the branch lines 7 at 4° C. approximately, the cooling gel must be refrigerated to a temperature of minus 30° C., and the housing 42 must be provided with an insulating layer 44 on its outside. The wall 45 of the cooling unit 41 facing the storage system 4 is provided with regularly spaced slits 46 whose opening cross-sections can be varied by shifting a shutter 48 provided with corresponding openings 47. The wall 45 and the shutter 48 must be made of a material with low thermal conductivity, and must be sufficiently strong in order to ensure that the temperature of the fluid fractions does not drop below the permissible minimum.

The shutter 48 may be actuated by a thermostat 49, for instance, a bimetallic element, which will keep the fluid fractions sufficiently cool even if the cooling effect of the cooling gel is diminishing. In the beginning, when the temperature of the cooling medium is very low, the shutter is closed almost completely, such that the fluid fractions are subject only to mild cooling; as the cooling medium loses its cooling effect, the shutter is opened correspondingly.

The device shown in FIGS. 3 to 5 has only one drive motor 50, which drives a cable 61 guided by rollers 60 of the piston 19 of the reciprocating pump 17 via the travelling part 52 of a spindle drive 51. Via a reducing gear 53 shown in FIG. 3, actuating a camshaft 55 by means of a ratchet wheel 54, squeezer levers 56 attached to the main housing 34 are actuated, each such lever 56 being lifted by a cam 57 of the camshaft 55, thus giving access to one of the branch lines 7 for receiving a fluid fraction. After the fluid fraction has entered each branch line 7 is clamped shut only in one place by a squeezer lever 56, the adhesive forces acting in the lines preventing the fractions from mixing upon a change in position of the case. The individual cams 57 actuating the squeezer levers 56 are positioned on the camshaft 55 basically along two helices, and are spaced 15 degrees apart.

In order to withdraw the individual fractions of the fluid the drive 21 of the reciprocating pump 17 can be reversed, the branch line which was filled first now being emptied first, and the direction of rotation of the camshaft being maintained.

After removal of the cooling unit 41 the line may be emptied by actuating a knob or crank 58 cooperating with the suction and pressure units 3 and 15 and the control element 20.

If samples are not taken continuously, it is recommended to use an electronic control system for the device, into which can be entered an individual sequencing program via a display 59. During a standstill of the suction unit 3 between two fluid withdrawals, blood clotting at the needle inserted in the bloodstream may be prevented by the addition of small doses of heparin via a small auxiliary pump. For this purpose the receiving vessel 25 could be used, which would only have to be furnished with a suitable driving means.

I claim:

1. A device for withdrawing body fluids, such as blood, urine, tissue fluid, comprising a withdrawal unit connected to a suction unit and a storage system which is situated between said suction unit and said withdrawal unit, said storage system comprises separable individual areas for respectively receiving and holding fractions of said body fluid gathered at certain sequential intervals, permitting said fluid fractions to be clearly identified with regard to their time of withdrawal, wherein said withdrawal unit is provided with an ingoing line for a liquid to be introduced into the body and an outgoing line for said body fluid to be gathered, and wherein said ingoing line is connected to a pressure unit.

2. A device according to claim 1, wherein said withdrawal unit is configured as a subcutaneous needle/catheter, or vascular needle, with two concentric channels, one of said channels is connected to said ingoing line and the other of said channels is connected to said outgoing line.

3. A device according to claim 1, comprising a reciprocating pump, being provided with a reservoir containing said liquid to be introduced into the body and serving as said pressure unit, and a suction chamber connected to said storage system and serving as said suction unit.

4. A device according to claim 3, comprising a receiving vessel of variable capacity, which is connected to said reservoir for said liquid to be introduced into the body via a flow-regulating element.

5. A device for withdrawing body fluids, such as blood, urine, tissue fluid, comprising a withdrawal unit connected to a suction unit and a storage system which is situated between said suction unit and said withdrawal unit, said storage system comprises separable individual areas for receiving and holding fractions of said body fluid gathered at certain intervals, permitting said fluid fractions to be clearly identified with regard to their time of withdrawal, wherein said withdrawal unit is provided with an ingoing line for a liquid to be introduced into the body and an outgoing line for said body fluid to be gathered, and wherein said ingoing line is connected to a pressure unit, said device further comprising drive units of said suction and said pressure unit, a control device for said storage system and a corresponding electronic control system, wherein said drive units, said control device and said electronic control system are located in a main housing, and wherein said storage system receiving said body fluid, said suction and pressure units and all connecting lines are located in a case which is detachable from said main housing.

6. A device according to claim 5, wherein said case is U-shaped, having halves being situated one on either side of said main housing, each including a number of individual branch lines, holding said fluid fractions.

7. A device according to claim 6, comprising a driving motor, which actuates said suction and pressure unit by means of a spindle drive, and which drives a camshaft via a reducing gear and a ratchet wheel, the cams of said camshaft cooperating with squeezer levers of said control device attached to said main housing, each of said cam-lifted lever giving access to one of said branch lines.

8. A device according to claim 6, wherein said branch lines and all flexible tubes of said storage system have small diameters, such that adhesive forces acting between the inner walls of said storage system and said body fluid are larger than exterior forces acting upon said device, such as gravitation or additional accelerating forces.

9. A device according to claim 6, wherein all said branch lines are connected to said suction unit via a manifold.

10. A device according to claim 5, wherein said case containing said storage system is connected to an adjustable cooling unit, which has a housing containing a cooling gel, and a wall of said housing facing said storage system is provided with openings having cross-sections, which are controlled via a thermostat, for admitting cooling air into said storage system.

11. A device according to claim 5, wherein said drive of said suction and pressure unit is reversible in order to withdraw said individual fluid fractions from said storage system.

12. A device according to claim 5, having a knob or crank cooperating with said suction and pressure unit and said control device of said storage system, in order to withdraw said individual fluid fractions from said storage system.

13. A device according to claim 5, wherein said withdrawal unit is configured as a subcutaneous needle/catheter, or vascular needle, with two concentric channels, one of said channels is connected to said ingoing line and the other of said channels is connected to said outgoing line.

14. A device according to claim 5, comprising a reciprocating pump, being provided with a reservoir containing said liquid to be introduced into the body and serving as said pressure unit, and a suction chamber connected to said storage system and serving as said suction unit.

15. A device according to claim 14, comprising a receiving vessel of variable capacity, which is connected to said reservoir for said liquid to be introduced into the body via a flow-regulating element.

16. A device according to claim 15, wherein said liquid to be introduced into the body is heparin and wherein said receiving vessel is provided with driving means ensuring a continuous supply of heparin to said withdrawal unit during a standstill of said suction and pressure unit.

17. An apparatus capable of withdrawing and storing separate samples of fluid taken from a body, said apparatus comprising:
 an insertion device for insertion into a body,
 a suction-generating means,
 a storage means connected between said insertion device and said suction-generating means, said storage means including a plurality of parallel pipes in which separate samples of body fluid withdrawn by said insertion device from said body can be stored,
 a pressure unit, and
 an inlet line connected between said pressure unit and said insertion device, said pressure unit being capable of supplying liquid to said inlet line and said insertion device for introduction into said body.

18. An apparatus capable of withdrawing and storing separate samples of fluid taken from a body, said apparatus comprising:
   an insertion device for insertion into a body,
   a suction-generating means,
   a storage means connected between said insertion device and said suction-generating means, said storage means including an elongated tube and means for introducing bubbles into said elongated tube for separating samples of body fluid therein which have been withdrawn by said insertion device from said body,
   a pressure unit, and
   an inlet line connected between said pressure unit and said insertion device, said pressure unit being capable of supplying liquid to said inlet line and said insertion device for introduction into said body.

* * * * *